United States Patent
Massengill

(10) Patent No.: US 8,950,864 B1
(45) Date of Patent: Feb. 10, 2015

(54) BRAIN DYSFUNCTION TESTING

(71) Applicant: R. Kemp Massengill, Leucadia, CA (US)

(72) Inventor: R. Kemp Massengill, Leucadia, CA (US)

(73) Assignee: Mednovus, Inc., Leucadia, CA (US)

( * ) Notice: Subject to any disclaimer, the term of this patent is extended or adjusted under 35 U.S.C. 154(b) by 0 days.

(21) Appl. No.: 14/197,336

(22) Filed: Mar. 5, 2014

Related U.S. Application Data

(60) Provisional application No. 61/965,770, filed on Feb. 7, 2014, provisional application No. 61/901,257, filed on Nov. 7, 2013, provisional application No. 61/959,749, filed on Aug. 30, 2013, provisional application No. 61/966,339, filed on Feb. 22, 2014.

(51) Int. Cl.
| | |
|---|---|
| *A61B 3/14* | (2006.01) |
| *A61B 3/00* | (2006.01) |
| *G06K 9/00* | (2006.01) |
| *A61B 5/00* | (2006.01) |
| *A61B 3/113* | (2006.01) |

(52) U.S. Cl.
CPC ............... *A61B 5/4064* (2013.01); *A61B 3/113* (2013.01)
USPC ............................ 351/209; 351/246; 382/117

(58) Field of Classification Search
USPC ......... 351/200, 209, 205, 206, 222, 236, 237, 351/245, 246; 382/109, 117
See application file for complete search history.

(56) References Cited

U.S. PATENT DOCUMENTS

| | | | |
|---|---|---|---|
| 5,123,726 | A | 6/1992 | Webster |
| 5,461,436 | A | 10/1995 | Campbell |
| 5,467,104 | A | 11/1995 | Furness, III et al. |
| 5,530,495 | A | 6/1996 | Lamprecht |
| 5,565,949 | A | 10/1996 | Kasha, Jr. |
| 5,589,897 | A | 12/1996 | Sinclair et al. |
| 5,596,339 | A | 1/1997 | Furness, III et al. |
| 5,623,925 | A | 4/1997 | Swenson et al. |

(Continued)

FOREIGN PATENT DOCUMENTS

| | | |
|---|---|---|
| DE | 19540802.0 | 5/1997 |
| GB | 2096791 | 10/1982 |

OTHER PUBLICATIONS

Hain, Timothy C.; Tracking Test; published at www.tchain.com; publication date unknown; pp. 1 through 7.

(Continued)

*Primary Examiner* — Thomas K Pham
*Assistant Examiner* — Brandi Thomas
(74) *Attorney, Agent, or Firm* — Mark D. Wieczorek; Mayer & Williams PC

(57) ABSTRACT

Systems and methods provided utilize gaze-tracking to measure quantitatively and accurately the ability of an athlete or other subject suspected of a concussion to maintain gaze within a figure-eight pattern during a given period of time. The fixation icon is presented at increasing velocities, with multiple staged velocities constituting the preferred embodiment. Utilizing a figure-eight pattern is preferred. Total tracking error time is tabulated during each velocity stage of the test protocol, and total tracking error time occurring during a given velocity stage is compared to a subject's baseline, e.g., a pre-season Individual Bioperformance Level (IBL) for that velocity stage. Systems and methods disclosed may be used to help prevent debilitating neurological damage in our athlete population, as well as having important military applications related to PTSD, and to other mission-critical performance endeavors.

30 Claims, 7 Drawing Sheets

(56) References Cited

U.S. PATENT DOCUMENTS

| | | |
|---|---|---|
| 5,659,327 A | 8/1997 | Furness, III et al. |
| 5,701,132 A | 12/1997 | Kollin et al. |
| 5,751,465 A | 5/1998 | Melville et al. |
| 5,825,460 A | 10/1998 | Kohayakawa |
| 5,864,384 A | 1/1999 | McClure et al. |
| 5,894,338 A | 4/1999 | Miehle et al. |
| 5,894,339 A | 4/1999 | Hosoi |
| 5,898,474 A | 4/1999 | McClure et al. |
| 5,903,397 A | 5/1999 | Melville et al. |
| 5,910,834 A | 6/1999 | McClure et al. |
| 5,942,954 A | 8/1999 | Galiana et al. |
| 5,946,075 A | 8/1999 | Horn |
| 5,969,871 A | 10/1999 | Tidwell et al. |
| 6,027,217 A | 2/2000 | McClure et al. |
| 6,033,076 A | 3/2000 | Braeuning et al. |
| 6,045,227 A | 4/2000 | Stewart et al. |
| 6,139,152 A | 10/2000 | Ghahramani |
| 6,145,991 A | 11/2000 | McClure et al. |
| 6,243,076 B1 | 6/2001 | Hatfield |
| 6,290,357 B1 | 9/2001 | Massengill et al. |
| 6,386,706 B1 | 5/2002 | McClure et al. |
| 6,533,417 B1 | 3/2003 | Sain |
| 6,592,222 B2 | 7/2003 | Massengill et al. |
| 6,743,022 B1 | 6/2004 | Sarel |
| 7,275,830 B2 | 10/2007 | Alster et al. |
| 7,753,526 B2 | 7/2010 | Todd |
| 2005/0165327 A1 | 7/2005 | Thibault et al. |
| 2008/0281187 A1 | 11/2008 | Massengill et al. |
| 2008/0309616 A1 | 12/2008 | Massengill |
| 2011/0205167 A1 | 8/2011 | Massengill |
| 2012/0105486 A1* | 5/2012 | Lankford et al. ............. 345/661 |
| 2012/0278766 A1 | 11/2012 | Massengill |

OTHER PUBLICATIONS

Massengill, R. Kemp; Fatigue Testing for Mission Critical Performance; U.S. Appl. No. 60/834,406; Jul. 31, 2006; 22 pages.

Spath, Patrice L.; Caring on Empty; Radiology Today; Jul. 3, 2006; pp. 20 through 24.

Zackon, David H.; Smooth Pursuit in Senescence; Acta Otolaryngol; 1987; pp. 290 through 297; vol. 104; Stockholm, Sweden.

Unknown Author; Industrial Safety—Cognitive Testing; Bowles-Langley Technology Co. publication; date unknown; one page.

Unknown Author; Richard Christian's life . . . ; Hopkins Medicine; Winter 2007; pp. 28 through 31.

Unknown Author; Workplace Impairment Test; CogState Ltd. publication at www.alert4work.com; date unknown; four pages.

* cited by examiner

BRAIN DYSFUNCTION TESTING

CROSS-REFERENCE TO RELATED APPLICATIONS

This application claims benefit of priority to:

U.S. Provisional Patent Application Ser. No. 61/959,749, filed Aug. 30, 2013, and entitled "SYSTEM AND METHOD FOR TESTING BRAIN DYSFUNCTION";

U.S. Provisional Patent Application Ser. No. 61/901,257, filed Nov. 7, 2013, and entitled "SYSTEM AND METHOD FOR TESTING BRAIN DYSFUNCTION";

U.S. Provisional Patent Application Ser. No. 61/965,770 filed Feb. 7, 2014, and entitled "BRAIN DYSFUNCTION TESTING"; and U.S. Provisional Patent Application Ser. No. 61/966,339, filed Feb. 22, 2014, and entitled "BRAIN DYSFUNCTION TESTING".

All of the above applications are hereby incorporated by reference in their entirety.

BACKGROUND OF THE INVENTION

Brain dysfunction can be acute or chronic. Acute brain dysfunction is generally caused by alcohol or drug intoxication, extreme fatigue, medical conditions such as cerebrovascular accidents, and sports and work-related concussions, as well as other conditions, including Post-Traumatic Stress Disorder (PTSD). Chronic brain dysfunction is medically related to age-related dementia, cerebral arteriosclerosis, Alzheimer's disease, Parkinson's disease, brain tumors, and other neurological and/or genetic disease entities.

Chronic brain dysfunction can also result from concussions, especially if these are repetitive. In some cases it has been postulated that PTSD may be related to an end product of the concussive effects of explosive devices, such as Improvised Explosive Devices (IED), at near range (although other causes are also postulated).

According to the U.S. Department of Veterans Affairs Center for PTSD, Defense and Veterans Brain Injury Center, and the Centers for Disease Control and Prevention:

Since 2011, more than 276,000 U.S. troops suffered some form of traumatic brain injury. PTSD occurs in 11-20% of veterans of the Iraq and Afghanistan wars, and was noted in some 30% of Viet Nam veterans.

Gaze-tracking deficiencies are known to be related to brain dysfunction. For example, when a highway patrolman asks a motorist suspected of impairment from drugs or alcohol to follow the officer's finger, this is an example of a method, albeit a crude and subjective one, for testing gaze tracking Gaze tracking deficiencies may also be related to glaucoma and other medical conditions.

Kasha and Massengill et al., have disclosed that errors in gaze tracking can be related to "fatigue"—but never in a sophisticated way, and neither suggests using sophisticated comparison techniques. Therefore, neither Kasha nor Massengill et al. disclose how fatigue can be objectively and accurately measured.

This Background is provided to introduce a brief context for the Summary and Detailed Description that follow. This Background is not intended to be an aid in determining the scope of the claimed subject matter, nor to be viewed as limiting the claimed subject matter to implementations that solve any or all of the disadvantages or problems presented above.

SUMMARY OF THE INVENTION

What is needed, and is of significant societal health benefit, are systems and methods for accurately quantifying gaze-tracking deficits in subjects suspected of brain damage. Systems and methods according to present principles provide a novel and practical quantification testing tool for individuals suspected of having acute or chronic brain dysfunction. In particular, what is provided is a simple-to-use yet highly-sophisticated system and method which supplies a mathematically-based solution for accurate gaze-tracking quantification for subjects suspected of brain dysfunction. Certain implementations may be especially useful for acute concussions, as well as for documenting late stage after-effects of concussion(s).

Systems and methods according to present principles allow the quantitative and accurate measurement of the time of tracking error relative to the total time of each stage of a formal test, and further allow comparison of these quantitative results to baseline performance values. The systems and methods provide for different and increasing velocities for each stage of the test in some implementations, and thus allow for the objective and accurate measurement of fatigue. The systems and methods correlate objective test results to a subject's baseline performance level, or to other athletes or other subjects participating in a given sport or activity, and disclose the compilation and display of the same numerically.

In one implementation, the disclosed systems and methods employ a head-mounted display with a video camera and gaze-tracker. The head may be in fixed relation to the display, such as in configurations employing goggles, eyeglasses, or helmets.

In another implementation, the head of the subject is not affixed or strapped to the display, but rather the head is unattached and is allowed to move. Hence, head movement can occur without movement of the display. For example, the testing may be performed using a display that is a tablet computer, a smart phone, or which employs a display that sits on a table. Such displays may then be coupled to the computing device driving the display in a wired or wireless fashion, e.g., using Bluetooth, IR, or the like. Said head movement, however, cannot be so drastic that the gaze-tracker cannot track the eye(s), as this would result in inability to perform testing. Thus, a limitation on head movement is that the gaze-tracker must be able to "see" the eye(s). For instance, the display can be viewed via goggle or eyeglasses configurations, such as, among others, but not exhaustively: a table-top positioned embodiment, a ground-positioned embodiment, a floor-positioned embodiment, or an articulating-arm positioned embodiment. Testing is initiated when the patient brings his or her head into position such that the gaze tracker is able to follow eye movement as a "blob", which is a target having a substantial areal extent and subtending a finite solid angle, which moves in its trajectory and is followed by a subject. It is to be noted that in these embodiments, if the head moves, the display instrument itself does not. A benefit of these configurations is that claustrophobia is generally eliminated for those subjects who might experience this unpleasant feeling when the head is strapped to an instrument. Also, the subject's hair is not tangled by straps or bands affixing the head. Those with long hair are often averse to hair tangles.

In more detail, to perform the methods described here, a system may be provided that includes a number of components. First, a display may be provided on which the blob is caused to move. A user monitor is also required to measure the subject's response, the user monitor being in one embodiment a tablet computer (which may also be the display) on which the user attempts to follow the blob. In another embodiment, the user monitor may be a gaze tracking device, configured to detect if a user's gaze is within a fixation zone defined by the blob or outside the fixation zone. The gaze tracker or an associated computing environment is also employed to determine the amount of time the gaze is within the fixation zone versus the amount of time the gaze is outside of the fixation zone. The display and gaze tracker are generally in the environment and vicinity of the subject—the computing environment may be located elsewhere and be in network communication with the display and gaze tracker. The display may be, e.g., a desktop, laptop, or tablet computer. The gaze tracker may be obtained from a number of commercially available sources. The gaze tracker or display, or both, may be head mounted. In one implementation, a gaze tracker is provided for each eye. In another implementation, only one goggle eyepiece in one gaze tracker is provided, this implementation relying on the fact that eye movement is usually concomitant. Alternatively, each may be not mounted to a subject's head, e.g., may be table-top or otherwise positioned, as noted above. In such case, the head of the subject may be located arbitrarily, so long as the gaze tracker is still able to follow the gaze (of at least one eye) of the subject and to determine the amount of time that gaze is within the fixation zone versus outside the fixation zone.

In yet other alternative embodiments, the display is mounted to the subject's head, but the gaze tracker is not. In yet a further embodiment, the gaze tracker is mounted to the subject's head, but the display is separate. Any of these combinations may be employed depending on the clinical situation. For example, for a pilot who already has a head-mounted display, use of the same may be particularly convenient. However, in a sports environment, e.g., on a football field, a table-top version may be advantageously employed. Other variations will also be understood by one of ordinary skill given this teaching.

Another implementation employs a touch-screen computer, and the subject attempts to trace with his or her finger within the spatial confines of a moving icon "blob" having an "areal extent" or just "extent" constituting a "fixation zone."

The systems and methods may provide a series of timed tests of pre-determined length(s), with each test displaying a moving icon "blob" constituting a "fixation zone" (significantly larger than a point, as discussed below), with sequential tests displaying this moving icon "blob" ("fixation zone") at a faster speed than the previous test. An associated computing environment reads instructions from a non-transitory computer-readable medium, the instructions causing the computing environment to operate the gaze-tracker and to measure a total elapsed time in which the subject's gaze stays within the spatial confines of the moving icon target "blob" ("fixation zone"), and also to measure the total elapsed time in which the subject's gaze is unable to stay within the boundaries of this moving icon target "blob" (such as 95% within the boundaries, and 5% outside the boundaries). The expression of this ratio of "inside/outside" the "blob" target is termed a "performance percentage". By comparing the performance percentage with that of a baseline, either previously measured for the subject or with a baseline of "normal subjects" (e.g., a mathematically significant number of normal subjects who have no history of concussion, alcohol or drug abuse, or of disease[s] affecting brain function), the relative performance of the subject individual may be determined. The test is repeated at multiple speeds of movement of the moving "fixation zone" "blob" icon, such that a performance percentage is obtained from the subject at each speed. It will be understood that various other methods and techniques, e.g., other measurements or indices, such as the total elapsed time gaze remains within the blob or outside the blob, may be employed using the gleaned data, besides strict use of a ratio.

It is noted that the moving icon target blob is not a point, but is of large enough size (i.e., subtends a large enough solid angle of the subject's vision, e.g., measured in steradians) that gaze tracking can vary within the moving fixation icon's blob spatial boundaries and still be considered error-free. Rather than attempting to track a point, within the "blob" are a large number of points, and the subject's eyes can move from one point to another within the blob without this movement constituting a fixation "error." This ability to shift gaze within the spatial confines of the blob without this constituting tracking error is a crucial innovative principle defining the operational implementation of the present invention. However, as the speed is increased in subsequent tests, it becomes increasingly more difficult to maintain gaze within the physical spatial confines of the moving blob icon.

Such systems and methods may be contrasted with those in which a single point or pixel or small set of pixels is used. For these prior systems, it is exceedingly difficult to obtain an accurate performance percentage from such a small point, or from a small icon. In contrast, the "fixation zone," i.e., the "blob" icon disclosed herein, is of sufficient size that variations of gaze can occur within the "blob" without constituting an "error." Only when the fixation gaze is outside the spatial confines of the "fixation zone" ("blob") is an "error" registered.

In one specific implementation, the following parameters are employed. It will be understood that other implementations will employ other values without departing from the spirit of the present principles. In one preferred embodiment of the present invention, seven speeds may be employed for gaze-tracking of the moving fixation icon, with each speed faster than the previous speed. Speeds may sequentially decrease as well, or may vary in non-monotonic fashions. Each speed may be employed for a test of a certain duration, e.g., such as 20 seconds in the preferred embodiment. A moving fixation target or "blob" may be provided having sufficient physical size such that a statistically significant number of normal subjects have a failure percentage of tracking (that is, for gaze to remain within the blob ("fixation zone") for the slowest speed of less than 1% of the elapsed time. The speed of the fastest test (e.g., icon fixation velocity IFV=7) is set so that only a small fraction of normal subjects—those with exceptional ability (such as some fighter pilots and talented athletes)—can track the moving fixation target at all well, so that most normal subjects fail. The speed is simply too fast for these subjects.

A figure-of-eight icon movement trajectory may be employed, as this shape efficiently tests all six eye muscles regulating gaze tracking. In this regard, it is noted that a figure-of-eight is in many cases superior to a circle as subjects find the figure-of-eight less boring (and thus a normal subject is less likely to fall into error simply because of inattention). Performance of the tests may be within a head-mounted display (HMD) incorporating a gaze tracker and video camera. In some cases, wireless transmission may be employed from the HMD to a computing environment programmed with appropriate software (wired connections may also be employed). No audio testing need be employed; in this way, testing can occur in even an extreme noise environment, such as in a sports stadium, a war zone, or during a highway interdiction as for alcohol or drug suspicion.

Multiple baseline screenings may be employed to make the testing more accurate, with some examples being as follows: baseline testing of an athlete before the season begins; baseline testing of an athlete after a strenuous workout in which no "head-shots" occurred; on-the-field testing of an athlete who was noted to have a "head-shot," said screening performed within a very short period of time (such as 30-90 seconds) after the athlete reaches the sidelines; baseline testing of an athlete at the end of the season, to determine if simply playing the sport induced a gaze-tracing deficit; baseline screening of military personnel soon after enlistment; baseline screening of military personnel before entering a war zone; baseline screening of military personnel after entering a war zone, but before any suspicion or complaints of PTSD; careful screening of military personnel suspected of PTSD; baseline screening if possible on a yearly basis of all active duty military personnel who have been in a war zone; baseline screening of all military personnel upon discharge from the military; if possible, baseline screening of all discharged military personnel on a 2-year basis, such as those eligible for VA medical care.

In another implementation, systems and methods may include performance of the testing method protocols employing a touch-screen computer, where the subject traces the moving icon "blob" with his/her finger, noted by the touch-screen computer's software to be either within the spatial confines of the "blob" or outside the spatial confines of the "blob." The moving icon may be, again, a figure-of-eight trajectory, or alternatively a circle, or other "blob" shape. Other details are similar to those disclosed herein.

Without intending to be limiting, it is noted that, in some cases, the HMD method may be advantageous, for one or more of the following reasons. The finger may have a tendency to drag on the computer touch-screen, giving fallacious information to the computer's software. The finger method may introduce "false positives", meaning that physical disabilities completely unrelated to aberrant brain dysfunction—for instance, tissue damage in the arm or hand—come into play, yielding failures that are not diagnostic of brain dysfunction.

Virtually any pattern may be employed for a user to follow. A figure-of-eight is indicated here purely for example purposes. However, it is noted that a figure-of-eight is, in essence, two circles, and is more interesting for the subject than following a circle. In this sense it is noted that following a circle is akin to trying to follow the blades of an oscillating fan. At a slow enough speed, a user can follow the fan accurately with his or her eyes. However, users will quickly become bored, or even fatigued, with the monotony of the fan's circular movement. Such may be especially apparent when the speed of rotation of the fan is increased (assuming the fan has a variable speed feature). Testing monotony can lead to false results, and, therefore, false conclusions. Following a circle, then, while useful, may not be in some implementations as advantageous as a figure-of-eight, which is efficient, non-boring, and tests all six muscles involved in eye movement.

Other patterns may also be employed, including trefoils, quatrefoils and multi-lobe generalizations of a figure-of-eight. Other patterns may also be used: zig-zags, rectangles, squares, etc. In these latter cases, however, the sharp corners in the patterns may lead to excess tracking failure even among normal subjects, and thus to potential difficulty in obtaining accurate baselines of "normal" subjects. In some implementations, e.g., a zigzag or rectangle shape, the sharp corners may be accounted for in the tracking software or hardware or both, by temporarily increasing the size of the blob at such corners or by allowing greater "forgiveness" in patient tracking errors at such points.

If the pattern trajectory is random, occasional motions in the outliers of the probability distribution used to generate the random patterns could also lead to difficulty in obtaining accurate baselines from "normal" subjects. Variability from one random pattern to the next could increase the scatter in data obtained from both normal and unknown subjects.

The same philosophy may apply to soldiers in war zones; namely, that a soldier with poor test results, especially upon repeated testing via the methods according to present principles, should generally not be returned into a war zone until, and unless, brain function has returned to the normal level. Impaired brain function renders correct life-and-death decisions difficult or impossible.

Another application is drug testing. In this regard it is noted that many drivers for which marijuana use is suspected may have the substance purged from their system by the time blood or urine analysis can be performed. Breathalyzer tests are often inconclusive, and, of course, are negative for alcohol consumption if such is not the case. Systems and methods according to present principles may be advantageously employed to non-invasively and non-intrusively detect impaired driving (or impairment during performance of other functions requiring motor skills, including piloting an aircraft or other vehicles). While individual baseline values may not be obtainable in such circumstances (unless the test subject has previously been tested), the subject may be tested against a baseline of normals or averages. For example, a minimum functional ability may be defined as a predetermined threshold, and if the test subject cannot perform at least to the level of the minimum functional ability, impairment may be presumed. The recent legalization of marijuana in several states including Colorado makes such testing particularly important.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

FIG. 4(A) illustrates a subject's gaze being determined to be within the spatial confines of a moving fixation icon blob, while

Like reference numerals refer to like elements throughout. Elements are not drawn to scale unless otherwise indicated.

DETAILED DESCRIPTION

Figure 1:
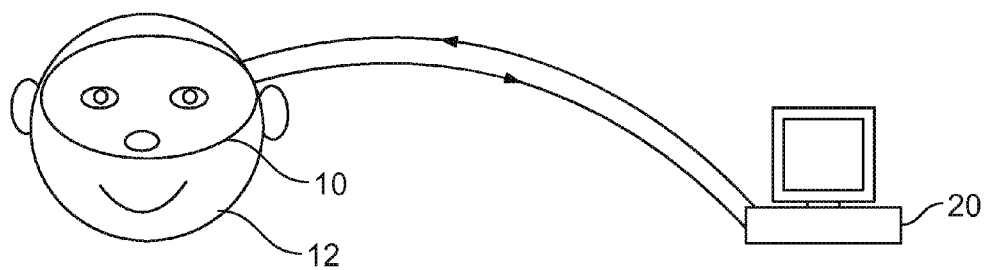
FIG. 1 illustrates a head-mounted display coupled to a computing environment providing analysis functionality.

Referring to FIG. 1, a subject 12 is illustrated having his or her brain function measured and monitored by a computing environment 20. The measuring and monitoring may be via a number of techniques, including use of a head-mounted display 10. The display 10 may be one in which the head is free to move with respect to the display screen, or one in which the head position is fixed with respect to the display, i.e., an apparatus employing goggles, glasses, or helmets. Other techniques will also be understood to be encompassed within present principles.

Figure 2:
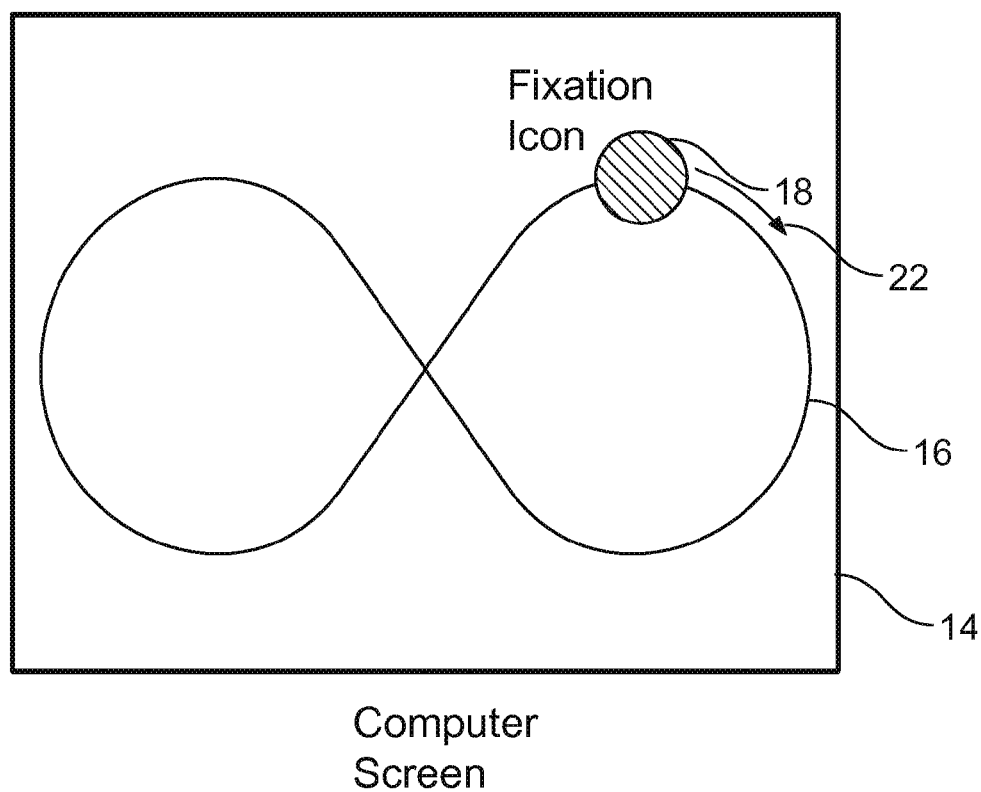
FIG. 2 illustrates a figure-of-eight moving icon trajectory on a computer screen, with a fixation "blob" icon of sufficient size (subtended visual angle, e.g., measured in steradians) to allow gaze fixation to vary within the spatial confines of the icon "blob" (i.e., the "fixation zone") without this varying constituting an "error."

As illustrated in FIG. 2, a computer screen 14 may portray a fixation icon "blob" (said blob constituting the "fixation zone") 18 traversing a path 16 as indicated by a trajectory speed arrow 22. The path 16 is indicated as a figure-of-eight, although it will be understood that other paths may also be employed as desired. The figure-of-eight has certain advantages, as has been described above.

Figure 3:
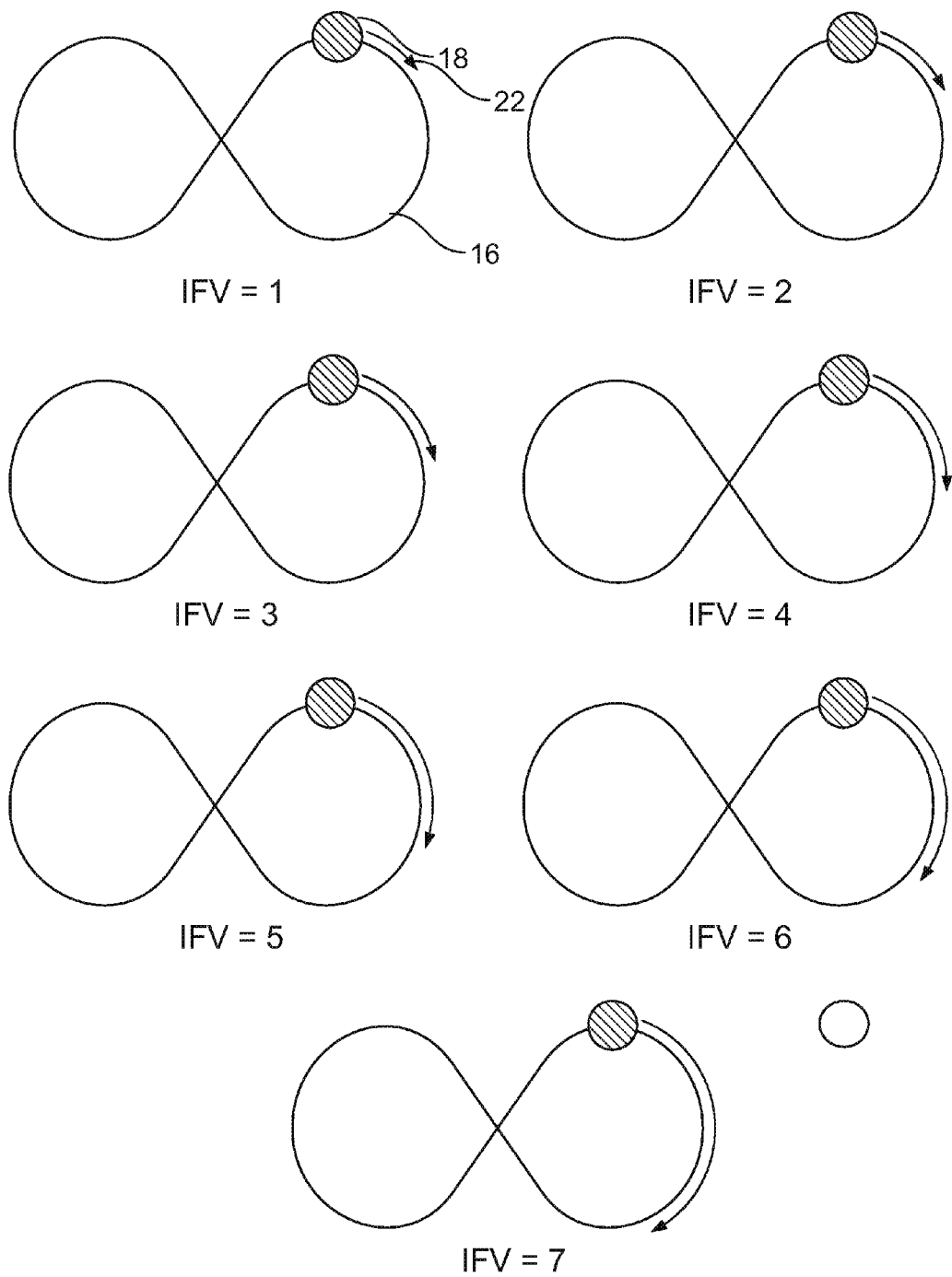
FIG. 3 illustrates increasing speed of movement of the moving "blob" icon, with one implementation as shown having seven sequentially-faster test speeds (other speeds may also be utilized).

FIG. 3 illustrates a number of icon fixation "blob" velocities traversing figure-of-eight paths, the velocities being indicated by the size of the trajectory speed arrow in each drawing. Moreover, each drawing has a legend indicating that the icon fixation velocity ("IFV") is represented by a numeral. The numeral itself is used as an index, with higher numerals indicating higher speeds.

Figure 4A:
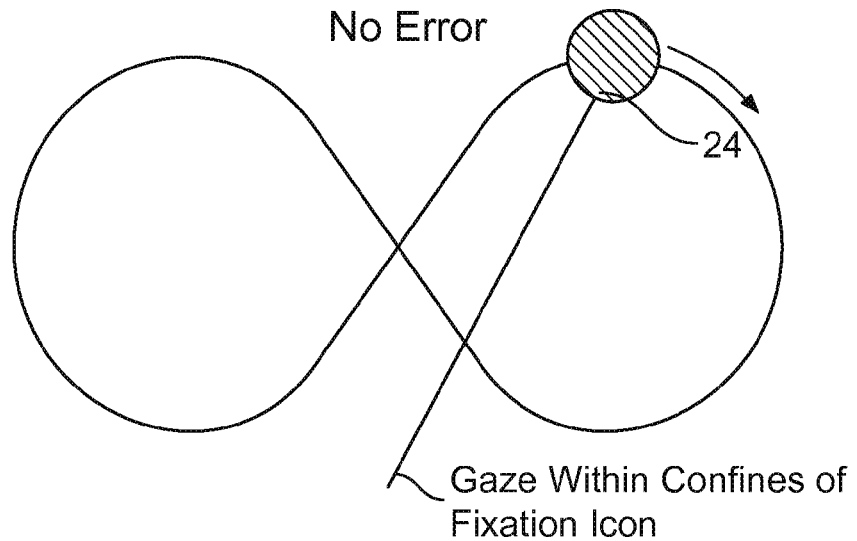
Figure 4B:
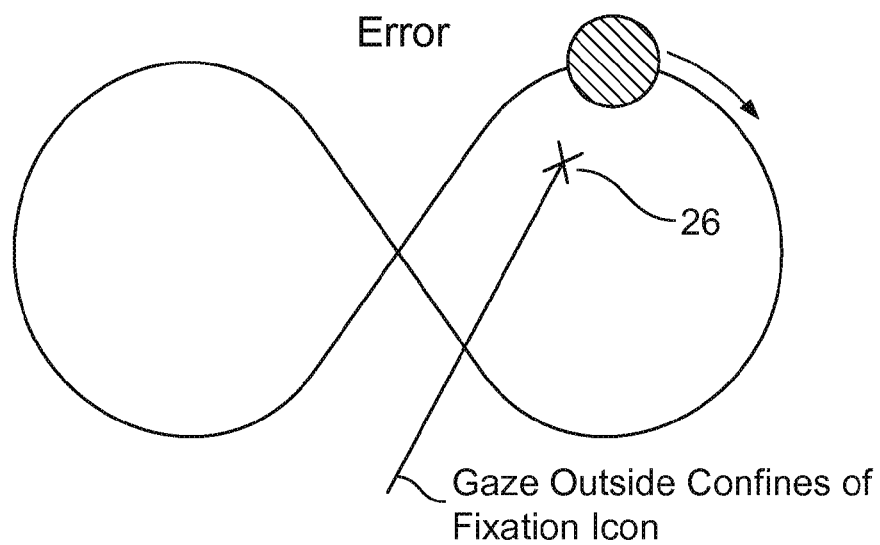
FIG. 4(B) illustrates the subject's gaze being determined to be outside the "blob", constituting fixation error.

FIGS. 4(A) and 4(B) illustrate how a user's gaze may be measured to be at a location 24 within the spatial confines of the fixation icon "blob" (4A) or at a location 26 outside the spatial confines of the -fixation icon 'blob" (4B). The time outside may be compared to the time inside in a number of ways, e.g., as a ratio or percentage, or using other comparison techniques.

Figure 5:
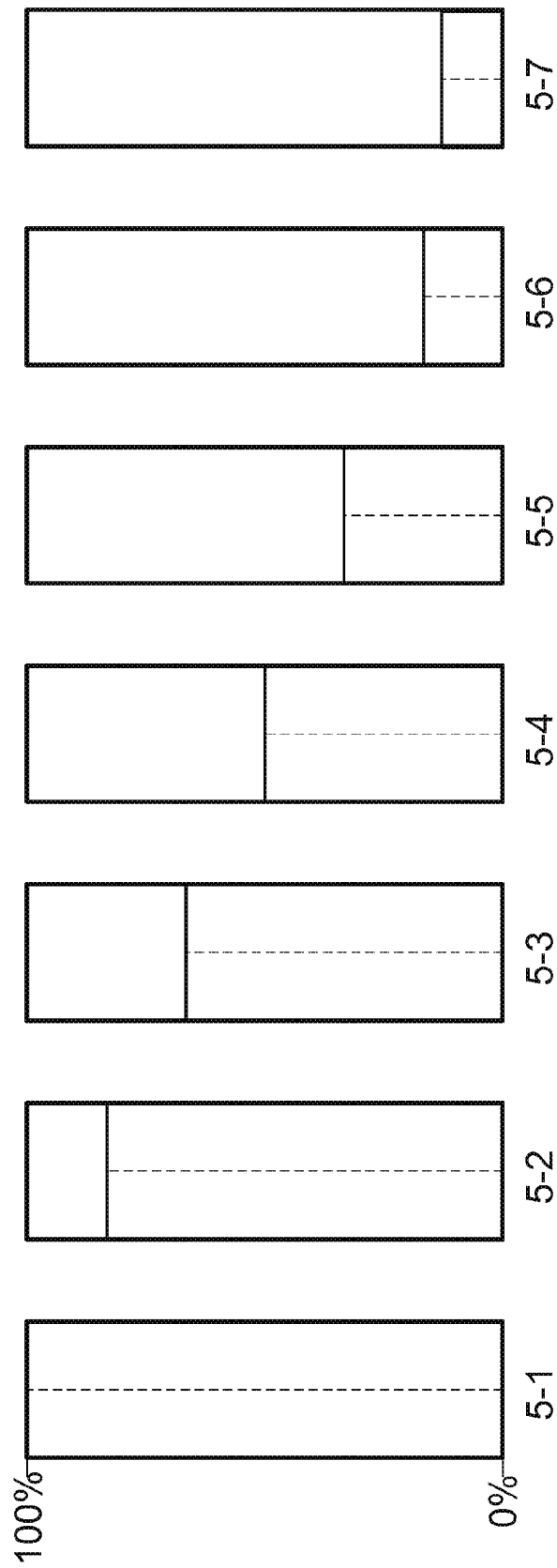
FIG. 5 illustrates baseline test performance results for "normal" subjects expressed as a percentage for each of seven test speeds.
Figure 6:
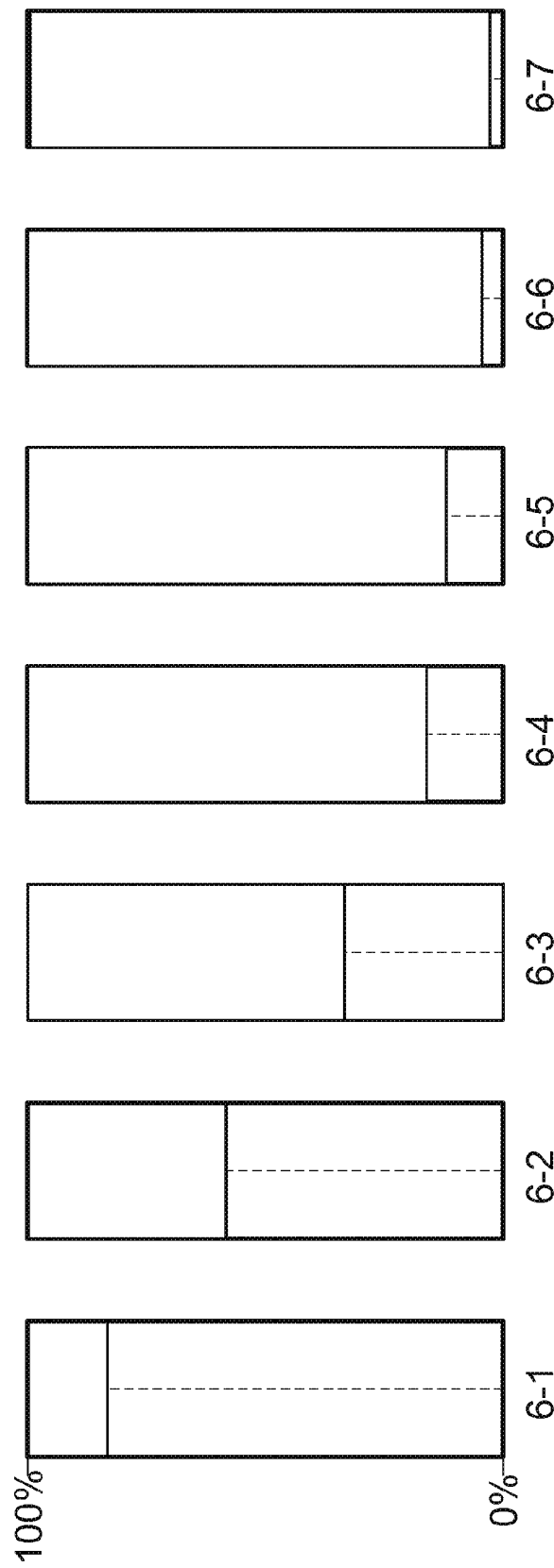
FIG. 6 illustrates test performance results of a previously "normal" subject with impaired brain function expressed as a percentage. This test performance may be compared with that of a subject's previous baseline testing results, and/or may also be compared to a baseline obtained from a significant number of "normal" subjects. In one implementation, for an athlete to be put back into a game, or before a subsequent game, the test performance generally should return to the baseline level for that athlete. The same principle applies to an airline pilot or to others performing mission-critical tasks.

FIG. 5 illustrates a number of results of testing. In the particular case of FIG. 5, the subject's results are "normal," indicating no impairment or reduction of brain function. In FIG. 6, the subject has performed the test following a potential or perceived reduction or impairment of brain function. In both cases, multiple test results are seen, with each result performed at a different icon fixation velocity or speed (although the same set of speeds may be used in both the tests of FIG. 5 and those of FIG. 6). At the slowest speed, and for the non-impaired subject, the result of which is portrayed by the histogram element at the far left, e.g., 5-1, the result is close to 100%. In other words, the user is able to track the moving fixation element and have his or her gaze nearly always stay within the "blob". Put another way, the subject's gaze may track the moving fixation element blob and not vary gaze from the same by more than a certain solid angle, e.g., a certain predetermined threshold number of steradians. Put yet another way, the user's gaze is attempting to stay within the spatial confines of the moving fixation element blob as the same moves around the path, the fixation element blob itself occupying a solid angle with respect to a point source at the user's eye of between about 0.02 and 0.09 steradians at a usual distance of a screen at arm's length, e.g., 12" to 32", or 15" to 28", or 20" to 28". Variations will be seen in these ranges, e.g., 0.04 to 0.08 steradians, 0.05 to 0.07 steradians, e.g., 0.6 steradians. (In this regard, it is noted that the field of view of a normal human is approximately $4.17=1.33\pi$ steradians.) The range may vary from a head-mounted display at a distance of an inch or two from the viewer's eyes, to a large screen located several dozen inches away. It will be understood that, despite the reference to solid angles, the blob ("fixation zone") may be of any shape, and the solid angle subtended thereby may be calculated appropriately. The shape of the object is irrelevant to its solid angle; all that matters is the total area of the object, projected onto the unit sphere.

In one exemplary implementation, where the blob is circular, the same may subtend an angle of about 14° at a distance of about 28 inches, with variations of, e.g., +/−20%, +/−10%, +/−5%, and so on, of the angle. Different distances will scale accordingly.

In FIG. 5, moving away from the leftmost histogram element, i.e., to the right, as icon fixation velocities or speeds increase, the user's gaze is able to stay within the "blob" or element to a lesser and lesser degree, i.e., to a lesser and lesser percentage. In other words, a user's gaze spends a lesser and lesser amount of time within the "blob", relative to outside the blob, as the speed increases. In FIG. 5, at the highest IVF, element 5-7, the user is only able to follow the moving icon "blob" with his or her gaze a very small fraction of the time, such as only a few percent. Comparing to FIG. 6, it may be seen that brain function clearly impacts the ability of a subject or patient to maintain gaze within the spatial confines of a moving fixation icon "blob". Even at the slowest speed, in this example, an impaired individual is unable to keep fixation gaze within the confines of the "blob" with normal accuracy (see deficit in histogram element 6-1 at the far left of FIG. 6, and then compare this to a normal histogram, as shown in FIG. 5-1). The ability of the subject to confine gaze within the spatial confines of the moving fixation icon "blob" is noticeably low compared to normal at element 6-4, decreases further at element 6-5, with further diminishment at element 6-6, and is nearly completely extinguished at element (and corresponding fixation speed) 6-7.

By comparing FIGS. 5 and 6 across the range of speeds, a clear reduction may be seen. (Note that in some cases, not every speed may show a reduction in performance between baseline and brain—dysfunctional states, due to statistical scatter; but the degradation will be visible generally, across the range of speeds.) Such may thus be employed to test for reductions in brain functionality or brain dysfunctions. For example, a rule may be instituted that a subject may not perform a task if the test cannot be performed with some threshold tracking capability maintained at speeds greater than half maximum. It will be understood to one of ordinary skill in the art given this teaching that numerous variations may be seen and are within the scope of the invention.

Figure 7:
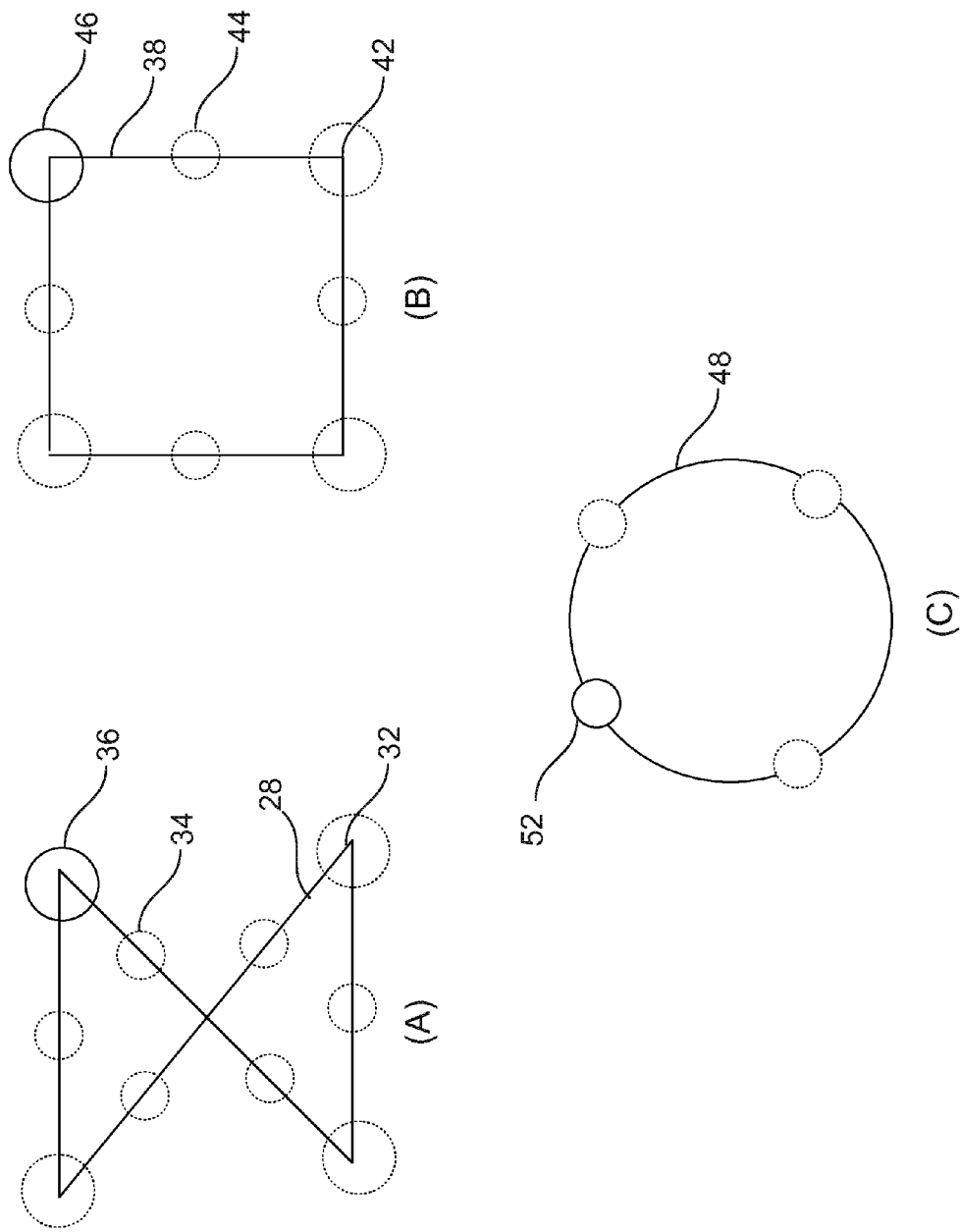
FIG. 7 illustrates blob enlargement at sharp corners.

FIG. 7 shows another implementation in which alternate patterns are considered, but where an adjustment is made to the size of the blob in order to accommodate inertia or other effects which may cause a subject to lose tracking of the blob at a sharp corner. For example, referring to FIG. 7(A), a closed zigzag pattern 28 is illustrated in which a blob 36 is shown in one position (the upper right) and where the blob is shown in various other positions as indicated by dotted lines. The blob 36 occupies these other positions (and positions in between) as the blob traverses the path. When the blob 36 is travelling in a generally straight direction, e.g., unswerving, it has a size indicated by the blob 34. When the blob is at sharp corners, e.g., corner 32, the blob may be provided in a larger size, as illustrated by the blob 36. A similar effect may be employed for a square path 38, as illustrated by FIG. 7(B). The blob 46 is enlarged at the corners, e.g., corner 42, but has a smaller size in between the sharp corners, e.g., at the position indicated by the smaller blob 44. In a circle or other path which does not have sharp corners, as illustrated by the circular path 48 of FIG. 7(C), the blob 52 maintains a constant size.

For paths with sharp corners, the enlarged blob allows a greater degree of "forgiveness," such that a user's gaze may (by inertia) continue moving in the direction it was going before encountering the sharp corner, but with a larger blob will not be deemed to be "out of the blob." And thus, the time out of the blob will not increase, unless of course the subject's gaze goes outside of even the larger blob. The enlargement of the blob may vary, and may be directly proportional to the sharpness of the corner. For example, if a user's gaze is caused to double back on itself, the size of the blob may be increased by 50 to 100%. If the zigzag is more gentle, e.g., a 90° angle, the size of the blob may only increase by 25 to 50%. For a still more gentle change, e.g., angular changes from 30 to 60°, the size of the blob may increase from about 5 to 25%.

The system and method may be fully implemented in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be inputted by way of an inserted memory chip, hard drive, flash drives, flash memory, optical media, magnetic media, or any other type of file—storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose.

In one implementation, a user of a smart phone or Wi-Fi—connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. In an implementation, an application may be employed to operate the method, such as by coupling to a head-mounted display or other display as disclosed above. The application running on the mobile device may then be enabled to transmit results using Wi-Fi, cellular, or other, to a server or other remote system, including to remote users operating other mobile devices. Transmission to a server may allow compiling of data at the server, such as to provide baseline or other aggregate response data.

Such a networked system may provide a suitable computing environment for an implementation in which a plurality of users provides separate inputs to the system and method. In the above system where brain function is monitored and measured, the plural inputs may allow plural patients to be monitored at one time.

Variations will be understood. For example, the display apparatus may be small enough and light enough such that during testing it can be held in the hands of the test subject or those of a test administrator. The display apparatus can be a tablet computer, or an alternative computer screen device, including a smart phone, with built-in video camera to perform gaze tracking. Alternatively, a video camera can be mounted upon the computer screen display. Relative motion between the subject being tested and the display screen may be minimized, so that the gaze tracking apparatus does not register false readings related to movement of the subject relative to the display screen. This is particularly true in implementations where the gaze tracker is not mounted to the subject's head, e.g., handheld implementations. Thus it is important that the test subject hold his or her head as steady as possible.

As noted above, a figure-eight pattern may preferably be employed because all six eye muscles (medial rectus muscle, lateral rectus muscle, inferior rectus muscle, superior rectus muscle, and inferior rectus muscle) must be properly functioning to have smooth and accurate gaze tracking of this pattern. But other non-preferred presentation patterns can be used, such as circles, triangles, and other shapes, including even random patterns as presented by the software associated with the goggle apparatus or computer screen. The elegance of the preferred-embodiment figure-eight pattern is that it is simple for the test subject to understand, and yet the most anatomically comprehensive, as testing all six muscles related to eye movement is efficiently carried out.

The figure-eight pattern is traversed by a fixation icon presented at increasing velocities, with the preferred embodiment consisting of seven staged velocities (FIGS. 5 and 6). These velocities, termed "Icon Fixation Velocities (IFV), are chosen after testing a statistically significant number (such as 300) of "normal" athletes, or other "normal" given subjects (pilots, military personnel, etc.)—i.e., with no known history of concussion.

The preferred embodiment tracking time to determine whether or not error occurs is 10-30 seconds, and in particular 20 seconds. As more experience over time is gained with the test protocol, it may be found that the testing time may be lengthened or shortened, and even to as little as 10 seconds.

In one embodiment, "trackable without error" may be defined for the 20-second preferred embodiment test as a cumulative total error of less than 0.4 second (i.e., less than 0.4 seconds is spent with the gaze outside the blob). This amount of error is considered "normal," as it relates to eye blinking, rather than neurological damage. On the other hand, a cumulative total error of five or more seconds indicates neurological deficit of at least a temporary nature.

In one implementation, utilizing the established Icon Fixation Velocities IFV 1-7, bioperformance testing of all athletes on a given team ensues during the off-season, and an Icon Fixation Velocity number is assigned to each athlete. This number represents the Individual Bioperformance Level (IBL) at which velocity tracking does not deviate from the histograms of "normal" subject athletes. To prevent an athlete from "faking" a low baseline IBL, athletes scoring IBL 3 or less should arbitrarily be prohibited from playing the potentially-violent sport in question. Motivated athletes will not "fake" this bioperformance test with such a severe penalty in place. And if an athlete validly cannot track within normal limits the first three Icon Fixation Velocities, occult and previously-unrecognized brain trauma may be the responsible culprit.

Now, if an athlete on the team scores IBL 4 or more on before-season testing, and is therefore allowed to participate in the sport in question, and subsequently undergoes a hit to the head (a "head-shot") with acute concussion suspected, that athlete may be immediately tested on the sidelines using a bioperfomance system according to present principles; and the fastest Icon Fixation Velocity IFV may be determined wherein during the 20-second test the athlete tracks consistent with his or her established baseline histograms (Individual Bioperformance Level IBL). Error is defined when the gaze tracker or video camera following tracking eye movements notes that the eye does not remain focused within the confines of the icon traversing the figure-eight pattern. It is emphasized that the traversing icon "blob" is therefore not a discrete point, but is rather of sufficient size that an error is readily recognized by the system's software when the test subject's gaze falls outside the confines of the fixation "blob" icon.

Advantageously systems and methods according to present principles require no audio, either related to the presentation of the figure-eight pattern, or related to the test protocol itself. The entire test procedure, then, can be silent, a great advantage especially in a full-throated, high-decibel stadium, such as that of the Green Bay Packers or the Pittsburgh Steelers. And it is noted that even high-school games can get very loud.

In any case, if the pre-season Individual Bioperformance Level ILB is not attained after a "head-shot," it is strongly recommended that the athlete in question not be put back into the game.

In some cases, an athlete may suffer a headshot but, when tested on the sideline immediately after the hit, his or her IBL matches (or even exceeds) his/her baseline. As there is so much at stake allowing a brain-damaged athlete to continue playing a sport in which subsequent head-shots could easily occur, and bearing in mind that edema of the brain ("brain swelling") may not be instantaneous, it is strongly recommended that the athlete in question be retested again, such as 15 minutes later, before going back into the game. Of course, if the baseline ILB is not attained, the athlete should be removed from the game. Generally, any athlete not attaining his or her baseline ILB should be removed from further competition, and thoroughly examined by a neurologist or other competent medical specialist. Complete testing, including even MRI or CT scanning, should be performed.

Any athlete with a witnessed head-shot should be tested before every single game remaining in the season, with comparison to the pre-season ILB, as well as to other testings during the course of that test subject's career.

Using a sufficiently large fixation icon minimizes lack of reliability of systems according to present principles. In particular, if the total error time is significantly increased compared to the Individual Bioperformance Level IBL for that athlete, as discussed above, the athlete SHOULD be considered to have suffered neurological damage and should be kept out of the game.

One further aspect of utilizing the present invention is related to ambient light. With head-mounted display systems completely blocking out ambient light, said ambient light is not a factor affecting the accuracy of IBL test scores. On the other hand, if ambient light enters the HMD system being employed, it is important that two sets of IBL scores be obtained, and comparisons made on a like-to-like ambient-light basis. For instance, IBL scores can be obtained in daylight, thereby creating one set of IBL scores. IBL scores can also be obtained during night-time conditions, such as at a night athletic contest, where the light tends to be less intense than broad daylight. This constitutes a second set of IBL scores. The same principle, i.e., two sets of IBL scores with one set related to daylight and the second set related to night-time, can be applied to touch-screen applications of the systems and methods disclosed here.

In other variations, rather than using gaze tracking to determine tracking error, an alternative non-preferred embodiment of the present invention is to use a touch-screen computer and have the subject track a moving icon traversing a figure-eight pattern with his/her finger. Tracking error is noted when the test subject's finger falls outside the confines of the fixation icon. Similar to the preferred embodiment of goggle-type apparati, the total elapsed tracking error time is noted and recorded, with comparisons to baseline test results.

In other variations, systems and methods according to present principles may be applied to other subjects suffering concussions, such as those suffering from Post-Traumatic Stress Disorder. In particular, soldiers suffering from Post-Traumatic Stress Disorder (PTSD) are now felt to be suffering from the delayed effect of concussion(s). These are believed to be related to the explosive force on the brain when a soldier is in close proximity to a detonated improvised Explosive Device (IED). The present systems and methods therefore have application in the battlefield in real-time, and afterwards—comparing a soldier's baseline to that obtained previously on that soldier, and to the norm of a representative and statistically significant group of soldiers. The preferred embodiment here again is a figure-eight pattern.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A method for testing eye muscle function of all six muscles involved in ocular movements to determine a reduction in brain function for an operator, said method comprising:

providing a display, a user input device, and an associated computer;

continuously displaying a movable blob around said display, for viewing by an operator, the blob being spatially confined within an extent when viewed by the operator such that the operator's gaze may vary within the spatial confines of the extent of the blob without constituting fixation error, the extent of the blob termed a fixation zone;

moving said blob on said display, under control of said computer, as said operator attempts to maintain gaze within said continuously displayed fixation zone, the moving performed in such a manner that all six eye muscles regulating eye movement are involved as said operator attempts to maintain gaze;

detecting, with said user input device, said operator's attempted gaze within or outside said continuously displayed fixation zone;

over a total time, determining a cumulative amount of time the gaze of the operator is within the fixation zone, and determining a cumulative amount of time the gaze of the operator is outside the fixation zone;

analyzing, with said computer, said operator's performance at following said continuously displayed fixation zone, said operator's performance including an ability of the operator to maintain gaze within the fixation zone constituting no fixation error versus outside the fixation zone constituting fixation error;

comparing said performance with a previously established baseline performance; and providing a result of said performance comparing.

2. The method recited in claim 1, wherein said user input device comprises a gaze tracking device associated with said display, and wherein said operator's attempted following of said continuously-displayed blob comprises tracking if the operator's gaze is directed within the fixation zone.

3. The method recited in claim 2, further comprising positioning said display in a fixed relationship to the head of said operator.

4. The method recited in claim 3, further comprising mounting said display to the head of said operator, said display being free to move with the head of said operator.

5. The method recited in claim 2, further comprising positioning the head of said operator relative to a positioning apparatus, said positioning apparatus remaining in a fixed position relative to said display.

6. The method recited in claim 1, wherein the analyzing includes calculating a ratio by dividing the cumulative amount of time the gaze of the operator is within the fixation zone by the total time, and comparing the ratio to a baseline value, wherein if the ratio is greater than the baseline value, a determination is made of no reduction in brain function.

7. The method recited in claim 1, wherein the moving said blob includes causing the blob to follow a "figure-of-eight" pattern.

8. The method recited in claim 1, wherein the movable blob having an extent when viewed by the operator in a range between about 0.02 steradians and 0.09 steradians, and wherein the sequentially altering includes moving the blob around said display at an angular speed with respect to the operator's eye of between about $\pi/8$ and $2\pi$ radians per second.

9. The method recited in claim 8, further comprising performing the steps of continuously displaying, moving, detecting, and determining the cumulative time at an initial angular speed of the continuously displayed blob, and then repeating the steps of continuously displaying, moving, detecting, and determining the cumulative time, at a different angular speed of the continuously displayed blob.

10. The method recited in claim 9, wherein the different angular speed is a higher angular speed, and further comprising comparing said operator's performance at said higher angular speed to said operator's performance at said initial angular speed, and determining a reduction in performance at a particular speed.

11. The method recited in claim 1, further comprising establishment of said previously established baseline performance by a method comprising:

providing a display, a user input device, and an associated computer;

continuously displaying a movable blob around said display, the movable blob being spatially confined within an extent when viewed by a test subject in a range between about 0.02 steradians and 0.09 steradians, an area of the blob within the range termed a fixation zone;

moving a location of said blob on said display, under control of said computer, as said test subject attempts to maintain gaze within said continuously displayed fixation zone;

detecting, with said user input device, said test subject's attempted gaze within said continuously displayed fixation zone;

over a total time, determining a cumulative amount of time the gaze of the test subject is within the fixation zone, and determining a cumulative amount of time the gaze of the test subject is outside the fixation zone; and analyzing, with said computer, said test subject's performance at following said continuously displayed fixation zone, said subject's performance including an ability of the test subject to maintain gaze within the fixation zone versus outside the fixation zone, to thereby establish said baseline performance.

12. The method recited in claim 11, wherein said at least one test subject and said operator suspected of having sustained a brain function reduction are the same person.

13. The method recited in claim 11, wherein establishment of a baseline performance includes repeating the steps for a plurality of test subjects.

14. The method recited in claim 1, further comprising establishing a plurality of discreet performance levels, constituting said baseline performance, said plurality of discreet performance levels ranging from a lowest performance level indicating the most likelihood of the presence of a reduction in brain function to a highest performance level indicating the least likelihood of the presence of a reduction in brain function.

15. The method recited in claim 14, wherein said determination of whether said operator's performance exhibits a reduced level of cerebral function indicating the incidence of a reduction in brain function comprises:

assigning said operator's performance to one of said discreet performance levels; and comparing said operator's performance level with a performance level previously established for said operator.

16. The method recited in claim 14, wherein said determination of whether said operator's performance exhibits a reduced level of brain function comprises:

assigning said operator's performance to one of said discreet performance levels; and comparing said operator's performance level with a performance level previously established as a minimum satisfactory performance level.

17. The method recited in claim 1, wherein the sequentially altering a location of said blob includes causing the blob to follow a circular pattern.

18. The method recited in claim 1, wherein the analyzing includes calculating a ratio by dividing the cumulative amount of time the gaze of the operator is outside the fixation zone by the total time, and comparing the ratio to a baseline value, wherein if the ratio is greater than the baseline value, then a determination is made of a reduction in brain function, and wherein the baseline value of the ratio is a function of a speed of the blob, varying from between about 0% and 5% at a lowest speed to between about 95% and 100% at the highest speed.

19. The method recited in claim 8, wherein the movable blob has an extent when viewed by the operator in a range between about 0.05 steradians and 0.07 steradians.

20. The method recited in claim 1, further comprising transmitting a result of the determining step to a remote mobile device or a remote server.

21. The method recited in claim 1, wherein the previously established baseline performance is a normal or average baseline performance constituting a minimum functional ability.

22. The method recited in claim 1, further comprising enlarging the extent of the blob according to a sharpness of a change in direction during the moving of said blob.

23. The method recited in claim 11, wherein the establishment of said previously established baseline performance further comprises:
    establishment of said previously established baseline performance according to claim 11, during a daytime condition, such that a daytime IBL is established; and
    establishment of said previously established baseline performance according to claim 11, during a daytime condition, such that a nighttime IBL is established.

24. The method recited in claim 23, further comprising selecting an IBL as the baseline performance for comparison to the results of the steps of the continuous displaying, the moving, the detecting, the determining, the analyzing, and the comparing, the daytime IBL being selected if the steps are performed during the daytime, and the nighttime IBL being selected if the steps are performed during the nighttime.

25. A system for testing eye muscle function of all six muscles involved in ocular movements to determine a reduction in brain function for an operator, said device comprising:
    a display;
    a user monitoring device, the user monitoring device configured to determine where an operator's gaze is pointing; and
    a computing environment, the computing environment programmed to:
        operate the display to continuously display a movable blob around said display, for viewing by an operator suspected of having sustained a reduction in brain function, the movable blob being spatially confined within an extent such that the operator's gaze may vary within the spatially confined extent without constituting fixation error, the spatially confined extent of the blob termed a fixation zone;
        operate the display to move said blob on said display, under control of said computer, as said operator attempts to maintain gaze within said fixation zone, the operating of the display to move said blob performed in such a manner that all six eye muscles regulating eye movement are involved as said operator attempts to maintain gaze at the blob;
        receive a signal from the user monitoring device to determine at a given time whether said operator's gaze is within the fixation zone of said continuously displayed blob, not constituting fixation error, or outside of the fixation zone of said continuously displayed blob, constituting fixation error;
        over a total time, calculate a cumulative amount of time the gaze of the operator is within the spatial confines of the fixation zone, not constituting fixation error, or calculate a cumulative amount of time the gaze of the operator is outside the spatial confines of the fixation zone, constituting fixation error;
        using the total time and either the cumulative amount of time the gaze of the operator is within the spatial confines of the fixation zone, or the cumulative amount of time the gaze of the operator is outside the spatial confines of the fixation zone, or both, to analyze said operator's performance at following said continuously displayed blob, said operator's performance including an ability of the operator to maintain gaze within the spatial confines of the fixation zone versus outside the spatial confines of the fixation zone;
        compare said performance with a previously established baseline performance; and
        provide a result of the performance comparison.

26. The system of claim 25 wherein the display is a head-mounted display.

27. The system of claim 25 wherein the display is not affixed to the head.

28. The system of claim 25 wherein the display and the user monitoring device are mounted within a unitary housing.

29. The system of claim 28 wherein the computing environment is further included within the unitary housing.

30. The system of claim 25 wherein the displayed is configured such that movable blob has an extent when viewed by the operator in a range between about 0.02 steradians and 0.09 steradians.

* * * * *